United States Patent [19]

Rossi

[11] 4,138,572
[45] Feb. 6, 1979

[54] MALONANILIC DERIVATIVES

[75] Inventor: Silvano Rossi, Milan, Italy

[73] Assignee: Roussel UCLAF, Paris, France

[21] Appl. No.: 731,988

[22] Filed: Oct. 13, 1976

Related U.S. Application Data

[60] Division of Ser. No. 276,242, Jul. 27, 1972, Pat. No. 4,001,408, which is a division of Ser. No. 41,757, Jun. 3, 1970, Pat. No. 3,984,398, which is a continuation of Ser. No. 689,810, Dec. 12, 1967, abandoned.

[51] Int. Cl.² .................................. C07C 103/147
[52] U.S. Cl. .................................. 560/43; 560/21; 560/22
[58] Field of Search ..................... 560/43, 21, 22

[56] References Cited

U.S. PATENT DOCUMENTS 3,984,398   10/1976   Rossi ..................... 260/239.3 B

OTHER PUBLICATIONS

Rossi, et al., "Tetrahedron", vol. 24, (Nov) 1968, pp. 6395-6409.
Phillips, J. Chem. Soc., vol. 172, pp. 2393 to 2399 (1928).
Shriner et al., J. Am. Chem. Soc., vol. 66, pp. 1810 to 1812 (1944).

*Primary Examiner*—John D. Randolph
*Assistant Examiner*—Robert T. Bond
*Attorney, Agent, or Firm*—Stevens, Davis, Miller & Mosher

[57] ABSTRACT

This invention relates to substituted 1,5-benzediazepines having the formula

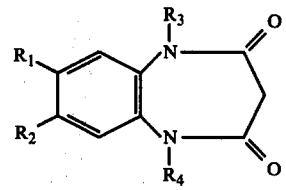

wherein
$R_1$ and $R_2$ are hydrogen or substituents
$R_3$ is hydrogen or substituents
$R_4$ is methyl or aryl group as well as the process of producing the same.

The compounds of the invention are tranquillizing analgesic, antipyretic and anti-inflammatory agents.

9 Claims, No Drawings

MALONANILIC DERIVATIVES

This is a division of application Ser. No. 276,242 filed July 27, 1972, now U.S. Pat. No. 4,001,408 issued Jan. 4, 1977, which in turn is a division of application Ser. No. 41,757 filed June 3, 1970, now U.S. Pat. No. 3,984,398 issued Oct. 5, 1976, which is a streamlined continuation of application Ser. No. 689,810 filed Dec. 12, 1967, now abandoned.

CLAIM OF PRIORITY

The right of priority is hereby claimed under the provisions of 35 USC 119, based on the Italian patent application No. 31,085 filed on Dec. 14, 1966.

OBJECTS OF THE INVENTION

An object of the present invention is the obtention of substituted 1,5-benzediazepines of the formula

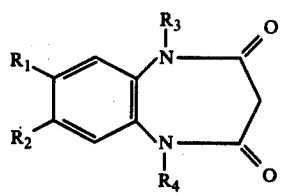

wherein
  $R_3$ is selected from the group consisting of hydrogen, alkyl, alkenyl, aralkyl, cycloalkyl, (cycloalkyl) alkyl
  $R_1$ is selected from the group consisting of hydroxy, methoxy, halogen, carbalkoxy wherein the alkyl group has from 1 to 4 carbon atoms when $R_4$ is methyl and $R_2$ is hydrogen
  or $R_2$ is selected from the group consisting of hydroxy, methoxy, halogen, carbalkoxy wherein the alkyl group has from 1 to 4 carbon atoms when $R_4$ is an aryl group and $R_1$ is hydrogen
  or $R_1$ and $R_2$ are hydrogen.

A further object of the present invention is the obtention of substituted 1,5-benzodiazepines of the formula

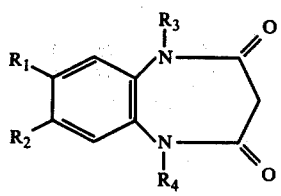

wherein
  $R_1$ and $R_2$ are selected from the group consisting of hydrogen, hydroxy, methoxy, halogen, and carbalkoxy wherein the alkyl group has from 1 to 4 carbon atoms
  $R_3$ is selected from the group consisting of hydrogen, alkyl, alkenyl, aralkyl, cycloalkyl (cycloalkyl) alkyl
  $R_4$ is selected from the group consisting of methyl and aryl.

A yet further object of the present invention is the obtention as preferred class of the N-methyl benzo 1,5-diazepines of the formula

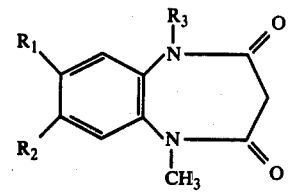

wherein
  $R_1$ is selected from the group consisting of hydrogen, hydroxy, methoxy, halogen and carbalkoxy wherein the alkyl group has from 1 to 4 carbon atoms,
  $R_2$ is hydrogen
  $R_3$ is selected from the group consisting of hydrogen, alkyl, alkenyl, aralkyl, cycloalkyl, and (cycloalkyl) alkyl.

Another object of the present invention is the obtention as preferred class of the N-aryl benzo 1,5-diazepines of the formula

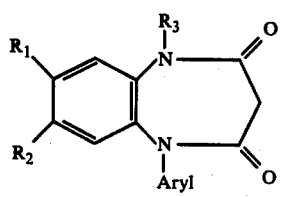

wherein
  $R_1$ is hydrogen
  $R_2$ is selected from the group consisting of hydrogen, hydroxy, methoxy, halogen, carbalkoxy wherein the alkyl group has from 1 to 4 carbon atoms
  $R_3$ is selected from the group consisting of hydrogen, alkyl, alkenyl, aralkyl, cycloalkyl and (cycloalkyi) alkyl.

Another object of the present invention is the development of a process for the production of any of the above defined benzo 1,5-diazepines which comprises the following steps (a) condensing a substituted or unsubstituted N-methyl or N-aryl 2-nitroaniline with a halide of a malenic acid mono alkyl ester wherein the alkyl group has from 1 to 3 carbon atoms so as to form a N-carbalkoxyacetyl N-methyl or aryl 2-nitro aniline:

(b) reducing in an acidic, neutral or basic medium the said nitro compound and producing a substituted or unsubstituted N-carbalkoxyacetyl N-methyl or N-aryl o-phenylene diamine;

(c) cyclising the N-carbalkoxyacetyl N-methyl or N-aryl o-phenylene diamine in strong acidic medium forming a substituted or unsubstituted N-methyl or N-aryl benzo-1-5-diazepine;

(d) treating if desired said benzo 1-5-diazepine with an alkylating, alkenylating, aralkylating, cycloalkylating or cycloalkyl alkylating agent in the presence of a metallating agent and recovering the desired N-methyl or N-aryl $N_1$-substituted benzo 1-5-diazepine.

Another object of the invention is the production of intermediate compounds produced during the process namely the N-carbalkoxyacetyl N-methyl or N-aryl 2-nitroanilines of the formula

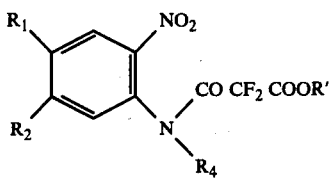

wherein
R₄ is selected from the group consisting of methyl and aryl
R' is an alkyl group having from 1 to 3 carbon atoms
R₁ and R₂ are selected from the group consisting of hydrogen, hydroxy, methoxy, halogen and carbalkoxy wherein the alkyl group has from 1 to 4 carbon atoms;
the N-carbalkoxy acetyl N-methyl or S-aryl o-phenylene diamines of the formula

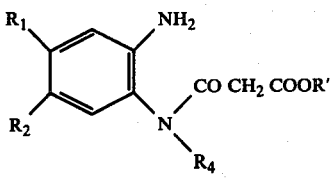

wherein the substituents $R_1$, $R_2$, $R_4$ and R' have the same meaning as above mentioned.

DESCRIPTION OF THE INVENTION

An object of the present invention is the obtention of new heterocyclic compounds of nitrogenous structure. This invention relates more particularly to benzo-1,5-diazepines with or without various substituents attached on the benzene nucleus and on the diazepine nucleus. It is specifically concerned with benzo-1,5-diazepines of the general formula(I):

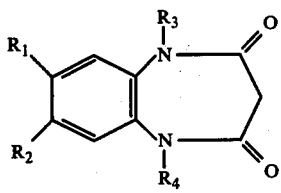

(I)

wherein
R₃ is hydrogen, an alkyl, aralkyl, alkenyl, cycloalkyl or (cycloalkyl) alkyl radical; R₁ is a halogen atom, a hydroxy radical, a methoxyl radical or a carbalkoxy radical, the alkyl group of which comprises 1 to 3 carbon atoms and R₂ is hydrogen, and in this case, R₄ is a methyl radical; or
R₁ is hydrogen;
R₂ is a halogen atom, a hydroxy radical, a methoxyl radical, or a carbalkoxy radical, the alkyl group of which comprises 1 to 3 carbon atoms, and in this case R₄ is an aryl radical; or R₁ and R₂ may be simultaneously hydrogen. In this formula, the alkyl radicals comprise 1 to 6 carbon atoms, the cycloalkyl radicals comprise 7 or 8 carbon atoms.

These compounds exhibit interesting pharmacological properties. They exert namely a depressing effect on the central nervous system.

Through the work of J. Buchi et al. benzo-1,5-diazepines substituted in position 3 were already known. These authors had searched after an analgesic or hypnotic effect, similar to that of barbiturics, and found that these products did not exhibit any sedative effect. Moreover, when they were substituted at nitrogen, they did exhibit little or not any analgesic effect.

The compounds corresponding to the general formula (I) differ from those previously known in that they exhibit strong tranquillizing anti-convulsive and analgesic effects. Moreover, they are endowed with an anti-inflammatory and anti-pyretic action.

More particularly, mention will be made of the compounds, wherein R₄ is an aryl group, the tranquillizing effect of which is at least equal to that of chlordiazepoxid, and the compounds wherein R₄ is a methyl radical, which are depressing agents of the central nervous system and namely:

1-methyl 7-chloro 1,2,4,5-tetrahydro 2,4-dioxo 3H-1,5-benzodiazepine;

1-methyl 1,2,4,5-tetrahydro 2,4-dioxo 3H-1,5-benzodiazepine;

1-methyl 5-n-propyl 1,2,4,5-tetrahydro 2,4-dioxo 3H-1,5-benzodiazepine;

1,5-dimethyl 1,2,4,5-tetrahydro 2,4-dioxo 3H-1,5-benzodiazepine;

1-methyl 7-methoxy 1,2,4,5-tetrahydro 2,4-dioxo 3H-1,5 benzodiazepine;

1-phenyl 1,2,4,5-tetrahydro 2,4-dioxo 3H-1,5-benzodiazepine;

1-phenyl 5-n-butyl 1,2,4,5-tetrahydro 2,4-dioxo 3H-1,5-benzodiazepine;

1-phenyl 8-chloro 1,2,4,5-tetrahydro 2,4-dioxo 3H-1,5 benzodiazepine;

1-phenyl 5-methylcyclopropyl 8-chloro 1,2,4,5-tetrahydro 2,4-dioxo 3H-1,5-benzodiazepine;

1-phenyl 5-allyl 8-chloro 1,2,4,5-tetrahydro 2,4-dioxo 3H-1,5-benzodiazepine;

1-phenyl 5-(2'-methyl-allyl) 8-chloro 1,2,4,5-tetrahydro 2,4-dioxo 3H-1,5-benzodiazepine.

Furthermore, these compounds distinguish themselves by a very low toxicity which ranges between 500 mg/kg and more than 2000 mg/kg in mice, intraperitoneally.

A further object of the invention is a process for the preparation of benzo-1,5-diazepines of the general formula:

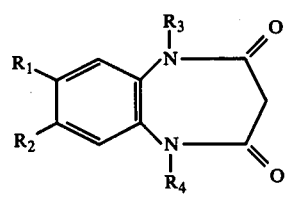

wherein
R₁ and/or R₂ are hydrogen, a halogen atom, an oxhydryl radical, a methoxyl radical or a carboxyl group, esterified with an alkanol having 1 to 3 carbon atoms;
R₃ is hydrogen, an alkyl, alkenyl, cycloalkyl, aralkyl or (cycloalkyl) alkyl radical; and
R₄ is a methyl or aryl radical, wherein a N-carbalkoxy acetyl o-nitro aniline, of the general formula:

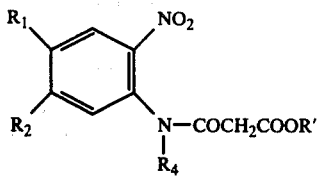

wherein $R_1$, $R_2$ and $R_4$ are as defined above; and $R'$ is an alkyl radical having 1 to 4 carbon atoms, is reacted with a reducing agent to form a N-carbalkoxy acetyl o-phenylene diamine, of the general formula:

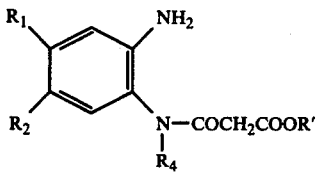

wherein the substituents $R_1$, $R_2$, $R_4$ and $R'$ are as defined hereinbefore, which is cyclized in acid medium into benzo-1,5-diazepine having the formula:

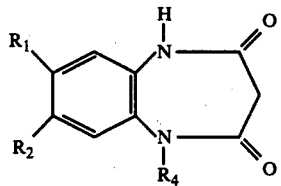

wherein the substituents $R_1$, $R_2$ and $R_4$ are as defined hereinbefore, which is reacted, if desired, with an alkylating, aralkylating, alkenylating, cycloalkylating or (cycloalkyl) alkylating agent, in basic medium to obtain the required N-substituted derivative.

Moreover, the process includes the following modes of operation:

(1) the cyclisation is effected by the action of a strong acid;
(2) the strong acid is a mineral acid, such as hydrochloric acid, sulfuric acid or perchloric acid;
(3) the alkylation of the benzo-1,5-diazepines is effected by the action of an alkyl halide or an alkyl sulfate in an inert solvent and in the presence of a metallation agent;
(4) the aralkylation of the benzo-1,5-diazepines is effected by acting an aralkyl halide in basic medium;
(5) the alkenylation of the benzo-1,5-diazepines is effected by acting an alkenyl halide in the presence of an organometallic derivative;
(6) the cycloalkylation of the benzo-1,5-diazepines is effected by acting a cycloalkyl halide in the presence of a metallation agent;
(7) the (cycloalkyl)alkylation of the benzo-1,5-diazepines is effected by means of a (cycloalkyl)alkyl halide, in the presence of a metallation agent;
(8) the metallation agent is an organic derivative of sodium or lithium;
(9) the metallation agent is an alkali-metal hydride or amide;
(10) the organometallic derivative is an alkali-metal alcoholate, such as sodium, potassium, lithium or cesium alcoholates;
(11) the reaction of substitution at nitrogen is effected at a temperature lying between 70 and 150° C;
(12) the reducing agent used to convert the N-$R_4$ N-carbalkoxy acetyl o-nitro anilines into N-$R_4$ N-carbalkoxy acetyl o-phenylene diamines is a reducing agent which acts in neutral alkaline or acid medium.

The reducing agent used to convert the N-$R_4$ N-carbalkoxy acetyl o-nitro anilines into N-$R_4$ N-carbalkoxy acetyl o-phenylene diamines is a reducing agent acting in neutral, alkaline or acid medium, depending upon the substituents attached on the benzene nucleus.

Suitable agents for this reduction include zinc, in the presence of alkali-metal hydroxide, ferrous sulfate in the presence of aqueous ammonia thiourea dioxide, in the presence of an alkali, sodium amalgam, aluminium amalgam, or ammonium sulfide, as agent acting in alkaline medium.

There may be mentioned hydrogen in the presence of a catalyst such as platinum oxide, rhenium oxide, nickel, Raney nickel or palladium or alkali-metal borohydride in the presence of a catalyst, such as palladium or copper, as agents acting in neutral medium.

When using a reducing agent acting in acid medium, the reduction of the nitro group and the cyclisation into benzodiazepine may be effected in one operation. Mention may be particularly made, in this case, of zinc in hydrochloric medium, iron in hydrochloric medium, tin or stannous chloride in hydrochloric medium, aluminium in the presence of sulfuric acid or zinc in the presence of ammonium chloride.

The starting compounds, the N-$R_4$ N-carbalkoxy acetyl o-nitro anilines may be obtained by the process consisting in condensing in an inert solvent a malonic mono-ester or a functional derivative of its acid function with a o-nitro aniline having the general formula:

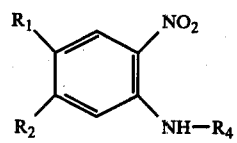

wherein the substituents $R_1$, $R_2$, and $R_4$ are as defined hereinbefore.

Further the invention includes also novel intermediates, the N-$R_4$ N-carbalkoxy acetyl o-nitro anilines, of the general formula:

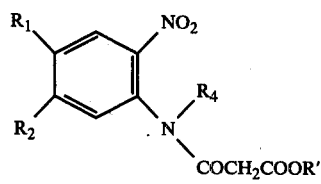

wherein $R_1$ and $R_2$ are hydrogen, a halogen, an oxhydryle radical, a methoxyl or a carboxyl group, esterified with an alkanol having 1 to 3 carbon atoms and $R'$ is an alkyl radical having 1 to 4 carbon atoms.

Moreover, the invention includes, as novel intermediates, the N-$R_4$ N-carbalkoxy acetyl o-phenylene diamine of the general formula:

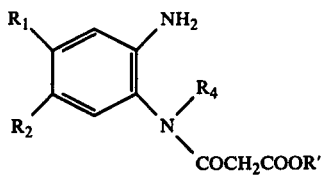

wherein $R_1$ and $R_2$ are hydrogen, a halogen, an oxhydryle radical, a methoxyl or a carboxyl group, esterified with an alkanol having 1 to 3 carbon atoms, and R' is an alkyl radical having 1 to 4 carbon atoms.

A further object of the invention is the variant of the process consisting in reducing the N-$R_4$ N-carbalkoxy acetyl o-nitro anilines, of the general formula:

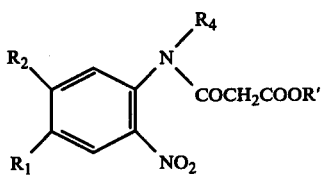

wherein the substituents $R_1$ and $R_2$ are hydrogen, a halogen, a hydroxy radical, a methoxy radical or a carboxyl group, esterified with an alkanol having 1 to 3 carbon atoms, and R' is an alkyl radical having 1 to 4 carbon atoms, by means of a reducing agent in acid medium to obtain directly the cyclisation into benzo-1,5-diazepine, of the general formula:

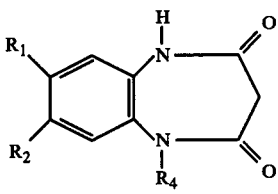

wherein $R_1$, $R_2$ and $R_4$ are as defined hereinbefore.

The following examples illustrate the invention, without being considered limitative in any manner. The temperatures are expressed in degrees centigrade.

Other modes of effecting the process or other reagents than those expressively indicated, may be used, without departing from the scope of the invention.

The products of the invention may be presented for administration to humans or animals, conditioned in a pharmaceutical form. The products may be administered parenterally, or orally, or rectally. They appear as drinkable or injectable solutions or suspensions, in ampoules or multi-dose flasks, as tablets, as pills, or as coated or progressively splitting tablets, as cachets, capsules, granules, syrup, drops and suppositories.

The useful range in human therapy is between 3 to 15 mg for a child and 15 to 100 mg for an adult, per day. In some instances, such as the treatment of psychic disorders the dose range can reach 200 mg per day.

The unit dosology ranges between 2 and 25 mg depending upon the mode of administration.

Because of their tranquilizing anti-convulsive, analgesic effects, the products of the invention may be used in human or veterinary therapy to treat emotional psychoses, anxiety, anguish, excitement or convulsion states. Their anti-inflammatory properties make them useful to prevent the functional disorders of organic expression, induced or increased by the psychical strain, neuralgia and pains of inflammatory or other origin.

PREPARATION OF THE STARTING MATERIALS

Among them, mention may be especially made of 2-nitro 5-methoxy diphenylamine, described by A. P. Kottenhahn J. Org. Chem. 28 (1963) 3 114, of 2-nitro N-methylaniline, described by Blanksma Recueil 21, 272, of 2-nitro 5-chloro diphenylamine, described by Laubenheimer Ber. 9, 771, of 2-nitro 4-methoxy N-methylaniline, described by A. M. Simonov J. Chim. Gener U.R.S.S. 21, 884 (1951), of o-nitro diphenylamine, described by Schopff Ber. 23, 1840, of 2-nitro 4-chloro N-methylaniline, described by Blanksma Recueil 21, 273, of 2-nitro 4-bromo N-methylaniline, described by Blanksma Recueil 21, 272, of 2,4-dinitro N-methylaniline, described by Leyman Ber. 15, 1 234, of 2-nitro 5-bromo diphenylamine, described by Jacobson Ann. 303, 323 and of 2-nitro 5-iodo diphenylamine, described by Jacobson Ann. 303, 339, or of 2,5-dinitro diphenylamine, described by R. V. Viggert J. Chim. Gener U.R.S.S. 30, 3 440 (1960).

EXAMPLE I

N-carbethoxy acetyl N-methyl o-nitro aniline 75 g of N-methyl o-nitro aniline and 70 g of monoethyl malonate (obtained according to M. FREUND, Ber. 17, 780, 1 884) are dissolved in 550 c.C. of benzene, the solution is agitated and 106 g of phosphorus pentachloride are added. while maintaining the temperature at 20°-23° C., this is agitated for three hours at room temperature, then heated for one hour at 70° C.; and yellow precipitate forms, which dissolves again, giving an orange solution; a water-ice mixture is added, while agitating, to obtain a volume of 1,500 c.c., keeping the temperature at 30° C.; the benzene phase is decanted off, washed with water, then with a saturated aqueous solution of sodium bicarbonate and finally with water, dried over sodium sulfate and evaporated under reduced pressure; the residue is purified by recrystallisation in the xylol-petroleum ether mixture (2,5-1). The compound melts at 54°-55° C.

| Analysis: $C_{12}H_{14}N_2O_5$ = 266.25 | | | |
|---|---|---|---|
| Calculated: | C % 54.13 | H % 5.30 | N % 10.52 |
| Found: | 54.02 | 5.23 | 10.77 |

As far as is known, this compound is not described in the literature.

Operating according to the preceding method and starting from N-methyl 2-nitro 4-chloro aniline, there is obtained N-carbethoxy acetyl N-methyl 2-nitro 4-chloro aniline, which melts at 45°-47° C.

| analysis: $C_{12}H_{13}N_2O_5Cl$ = 301.68 | | | |
|---|---|---|---|
| Calculated: | C % 47.93 | H % 4.36 | N % 9.32 |
| Found: | 48.11 | 12 4.56 | 9.30 |

As far as is known this compound is not described in the literature.

Operating according to the same method and starting from 3 g of N-methyl 2-nitro 4-methoxy aniline, there is obtained N-methyl N-carbethoxy acetyl 2-nitro 4-methoxy aniline.

As far as is known, this compound is not described in the literature.

Operating according to the same method and starting from 4 g of methyl 3-nitro 4-methylamino benzoate, there is obtained methyl 3-nitro 4(N-methyl N-carbethoxy acetyl)amino benzoate.

As far as is known, this compound is not described in the literature.

Operating according to the same method and starting from 1.75 g of 2-nitro 4-hydroxy N-methyl aniline there is obtained 2-nitro 4-hydroxy N-methyl N-carbethoxy acetyl aniline.

As far as is known, this compound is not described in the literature.

EXAMPLE II

N-carbethoxy acetyl 2-nitro 5-chloro diphenylamine 253.6 g of 2-nitro 5-chloro diphenylamine are dissolved in 1 500 c.c. of benzene, 187 g of mono-ethyl malonate are added, then, at room temperature, 224 g of phosphorus pentachloride are added, while agitating, to the mixture which is agitated for one hour at room temperature, progressively heated to a temperature of 75° C. within one hour and taken to reflux for five hours; this is cooled by adding the water-ice mixture, keeping the inner temperature at +30° C.; the benzene phase is decanted off, washed with water, then with a solution of sodium carbonate dried over sodium sulfate and evaporated under reduced pressure; the residue is purified bu recrystallisation in the xylene-petroleum ether mixture (1-1) to obtain N-carbethoxy acetyl 2-nitro 5-chloro diphenyl amine, melting at 88°–90° C.

| Analysis: $C_{17}H_{15}N_2O_5Cl$ = 362.74 | | | |
|---|---|---|---|
| Calculated: | C % 56.28 | H % 4.17 | N % 7.72 |
| Found: | 56.17 | 4.42 | 7.50 |

As far as is known, this compound is not described in the literature.

Operating according to the preceding method, starting from 2-nitro diphenylamine, there is obtained N-carbethoxy acetyl 2-nitro diphenylamine, melting at 63°–65° C.

| Analysis: $C_{27}H_{16}N_2O_5$ = 328.31 | | | |
|---|---|---|---|
| Calculated: | C % 62.19 | H % 4.91 | N % 8.53 |
| Found: | 61.98 | 5.19 | 8.40 |

As far as is known, this compound is not described in the literature.

Starting from 17 g of 2-nitro 5-methoxy diphenylamine, and operating according to the mode of operation of example II, there is obtained N-carbethoxy acetyl 2-nitro 5-methoxy diphenylamine.

As far as is known, this compound is not described in the literature.

Starting from 6 g of 2-nitro 5-chloro N(p-tolyl)aniline according to the mode of operation of example II, there is obtained N-carbethoxy acetyl 2-nitro 5-chloro N(p-tolyl) aniline.

As far as is known, this compound is not described in the literature.

EXAMPLE III

N-carbethoxy acetyl N-methyl o-phenylene diamine 11 g of N-carbethoxy acetyl N-methyl o-nitro aniline are admixed with 16.2 g of powdered zinc, and 100 g of cracked ice are added, whilst agitating; 62 c.c. of concentrated hydrochloric acid, diluted with 250 c.c. of iced water, are then added, and this is cooled to −5–10° C. for ten to fifteen minutes; the temperature is allowed to raise again to +5° C. within thirty minutes, this is filtered, the filtrate is alkalinized with ammonium hydroxide and extracted with chloroform; the chloroformic phases are washed with water, dried over sodium sulfate and evaporated under reduced pressure; the residue is dissolved in 30 c.c. of xylene and the solution is kept overnight at −10° C.; the formed precipitate is washed with ether and recrystallized in xylene, to obtain N-carbethoxy acetyl N-methyl o-phenylene diamine, melting at 63°–64° C.

| Analysis: $C_{12}H_{16}N_2O_3$ = 236.26 | | | |
|---|---|---|---|
| Calculated: | C % 61.00 | H % 6.83 | N % 11.86 |
| Found: | 61.19 | 6.98 | 12.00 |

As far as known, this compound is not described in the literature.

Operating according to the preceding method, and starting from N-carbethoxy acetyl N-methyl o-nitro p-chloro aniline, there is obtained N-carbethoxy acetyl N-methyl 4-chloro o-phenylene diamine, melting at 112°–114° C.

| Analysis: $C_{12}H_{15}N_2O_3Cl$ = 271.69 | | | |
|---|---|---|---|
| Calculated: | C % 53.24 | H % 5.59 | N % 10.35 |
| Found: | 53.35 | 5.61 | 10.45 |

As far as is known this compound is not described in the literature.

EXAMPLE IV

N-carbethoxy acetyl N-methyl 4-methoxy o-phenylene diamine 5 g of N-carbethoxy acetyl N-methyl d-methoxy 2-nitro aniline are dissolved in 50 cc. of hot ethanol. After cooling 15 cmc. of water and 3 cc. of a 2% solution of palladium chloride are added. Then 5 c.c. of a 20% aqueous solution of sodium borohydride are introduced, while cooling. This is agitated for thiry minutes, without allowing the temperature to exceed 40° C. Then the excess of reagent is decomposed by acidifying to pH =2 with hydrochloric acid. After cessation of the gaseous omission, the medium is filtered then neutralised with addition of ammonium hydroxide N-carbethoxy acetyl N-methyl 4-methoxy o-phenylene diamine precipitates. The precipitate is filtered, washed with water, filtered with suction and dried. Thus, there are obtained 3.75 g of N-carbethoxy acetyl N-methyl 4-methoxy o-phenylene diamine, which is purified by recrystallization in ethanol.

As far as is known, this compound is not described in the literature.

Methyl 4(N-carbethoxy acetyl N-methylamino)-3-amino benzoate

Operating in the same manner, and starting from 3 g of methyl amino 4(N-carbethoxy acetyl N-methyl) 3-nitro benzoate, there is obtained 1.90 g of methyl 4(N-carbethoxy acetyl methylamino) 3-amino benzoate.

As far as is known, this compound is not described in the literature.

EXAMPLE V

N-carbethoxy acetyl N-phenyl o-phenylene diamine 4 g of N-carbethoxy acetyl 2-nitro diphenylamine are dissolved in 40 c.c. of methanol, 10 c.c. of water, then 2 c.c. of a 2% solution of palladium chloride and 5 c.c. of a 20% solution of sodium borohydride are added thereto. This is stirred, while cooling for thirty minutes. Then the excess of reagent is decomposed by acidifying to pH 2 with hydrochloric acid. The blackish suspension is filtered, then the filtrate is neutralized with ammonium hydroxide. The precipitate is extracted three times with 20 c.c. of methylenechloride. The methylenic phases are combined, washed with water, then dried over sodium sulfate and evaporated to dryness in vacuo.

The (N-carbethoxy acetyl N-phenyl) o-phenylene diamine obtained is purified by recrystallization in the hot and in the cold in isopropyl ether.

As far as is known, this compound is not described in the literature.

In the same manner, starting from 4.5 g of N-carbethoxy acetyl 2-nitro 5-methoxy diphenylamine, there is obtained (N-carbethoxy acetyl N-phenyl) 5-methoxy o-phenylene diamine.

As far as is known, this compound is not described in the literature.

EXAMPLE VI

N-carbethoxy acetyl N-phenyl 5-chloro o-phenylene diamine 2 g of N-carbethoxy acetyl 5-chloro 2-nitro diphenylamine are dissolved in 60 c.c. of ethanol. 0.1 g of 5% palladised charcoal, is added. Hydrogen is introduced under ordinary pressure after purging the solution with nitrogen. The introduction of hydrogen is continued for thirty minutes until cessation of the absorption.

Then, the catalyst is filtered off. The alcoholic solution is concentrated under inert atmosphere. The dry residue is taken up with 10 c.c. of hot isopropyl ether. By cooling, N-carbethoxy acetyl N-phenyl 5-chloro o-phenylene diamine precipitates in a crystallized form.

EXAMPLE VII 1-phenyl 1,2,4,5-tetrahydro 2,4-dioxo 3H-1,5-benzodiazepine, ($R_1$, $R_2$ = H $R_4$ = $O_6H_5$ and $R_3$=H)

2.1 g of N-carbethoxy-acetyl N-phenyl o-phenylene diamine (with $R_1$ and $R_2$ = H and R' = $O_2H_5$), obtained in example VI, are dissolved in 30 c.c. of 4N hydrochloric acid by heating gently. The heating is maintained for a few minutes and diazepine separates. This is left at the room temperatutre for six hours, then filtered with suction and purified by crystallization in ethanol at 95° C. m.p. = 271°–272° C.

| Analysis: $C_{15}H_{12}N_2O_2$ | | | |
|---|---|---|---|
| Calculated: | C % 71.41 | H % 4.50 | N % 11.11 |
| found: | 71.57 | 4.90 | 11.16 |

As far as is known, this compound is not described in the literature.

EXAMPLE VIII 1-phenyl 5-n butyl 1,2,4,5-tetrahydro 2,4-dioxo 3H-1,5-benzodiazepine, I, (with $R_3$ = n-$C_4H_9$, $R_1$= H, $R_2$ = H and $R_4$ = $O_6H_5$)

To an alcoholic solution of sodium ethylate, obtained from 0.12 g of sodium and 50 c.c. of anhydrous ethanol, there are added 1.25 g of 1-phenyl 1,2,4,5-tetrahydro 2,4-dioxo 3H-1,5-benzodiazepine, I (with $R_1$ and $R_2$ = $H, R_4$=$C_6H_5$, obtained in the example VII, then 2.64 g of n-butyl bromide. The mixture is refluxed for twenty hours, then the solvent is evaporated under reduced pressure and the residue is taken up with 30 c.c. of 10% sodium hydroxyde. It is left, whilst agitating, at room temperature for one hour, then the precipitate is filtered with suction and purified by crystallisation in isopropanol; m.p. = 122° – 124° C.

| Analysis: $C_{19}H_{20}N_2O_2$ | | | |
|---|---|---|---|
| calculated: | C % 73.98 | H % 6.54 | N % 9.08 |
| found: | 73.78 | 6.63 | 9.17 |

As far as is known, this compound is not described in the literature.

EXAMPLE IX 1-phenyl 5-methyl 1,2,4,5-tetrahydro 2,4-dioxo 3H-1,5-benzodiazepine ($R_1$ and $R_2$ =H, $R_3$ = $OH_5$, $R_4$ =$O_6H_5$)

Starting from 1-phenyl 1,2,4,5-tetrahydro 2,4-dioxo 3H-1,5-benzodiazepine, obtained in the example VIII, by acting methyl chloride in the presence of sodium ethanolate, there is obtained 1-phenyl 5-methyl 1,2,4,5-tetrahydro 2,4-dioxo 3H-1,5-benzodiazepine, melting at 144°–146° C. after recrystallisation in isopropanol.

| Analysis: $C_{16}H_{14}N_2O_2$ | | | |
|---|---|---|---|
| Calculated: | C % 72.16 | H % 5.50 | N % 10.52 |
| Found: | 72.31 | 5.51 | 10.51 |

As far as is known, this compound is not described in the literature.

EXAMPLE X 1-phenyl 8-chloro 1,2,4,5-tetrahydro 2,4-dioxo 3H-1,5-benzodiazepine (with $R_1$ = H, $R_2$ = Cl, $R_3$ = H and $R_4$ = $O_6H_5$)

18 g of N-carbethoxy acetyl 2-nitro 5-chloro diphenylamine, obtained in the example II, are suspended in 190 c.c. of ethanol, admixed with 93 c.c. of hydrochloric acid, treated, while stirring, with 12.5 g of powdered zinc at the temperature of 15°–20° C. for about half an hour. The nitro derivative dissolves progressively and immediately afterwards, diazepine separates out. After further agitation for half an hour, at room temperature, this is diluted with 500 c.c. of water and the precipitate is filtered with suction after standing for two hours. The crude product is treated with 500 c.c. of 10% caustic soda; the insoluble matter is filtered off and a precipitate formed by acidifying the filtrate with hydrochloric acid. Finally, this is purified by cristallisation in acetic acid m.p. 290°-292° C.

| Analysis: $C_{15}H_{11}N_2O_2Cl$ | | | |
|---|---|---|---|
| Calculated: | C % 62.83 | H % 3.87 | N % 9.77 |
| Found: | 63.08 | 4.12 | 9.95 |

As far as is known, this compound is not described in the literature.

EXAMPLE XI

Starting from 1-phenyl 8-chloro 1,2,4,5-tetrahydro 2,4-dioxo 3H-1,5-benzodiazepine(obtained according to the example XI) and from a halide, and operating according to the example X, there is obtained 1-phenyl 5-methyl 8-chloro 1,2,4,5-tetrahydo 2,4-dioxo 3H-1,5-benzodiazepine, melting at 166°-168° C. after recrystallisation in 50% ethanol.

Starting from 1-phenyl 8-chloro 1,2,4,5-tetrahydro 2,4-dioxo 3H-1,5-benzodiazepine (obtained according to the example XI) and from a benzyl halide, operating according to the process of the example IX, there is obtained 1-phenyl 5-benzyl 8-chloro 1,2,4,5-tetrahydro 2,4-dioxo 3H-1,5-benzodiazepine, melting at 173°-175° C. after recrystallisation in isopropanol.

| Analysis: $C_{22}H_{17}ClN_2O_2$ | | | |
|---|---|---|---|
| Calculated: | C % 70.12 | H % 4.55 | N % 7.44 |
| Found: | 69.88 | 4.80 | 7.34 |

As far as is known, this compound is not described in the literature.

EXAMPLE XII 1-methyl 7-chlor 1,2,4,5-tetrahydro 2,4-diketo 3H-1,5-benzodiazepine ($R_1$ = Cl, $R_2$ = H, $R_3$ = H, $R_4$ = $CH_3$)

7 g of N-carbethoxy acetyl N-methyl-4-chloro-o-phenylene diamine, obtained in the example III (melting point; 112°-114° C. after recrystallisation in ethanol) are suspended, while agitating, in 50 c.c. of diluted hydrochloric acid (25 c.c. of concentrated hydrochloric acid, mixed with 35 c.c. of water). The product dissolves slowly and soon afterwards, the precipitate of diazepine appears. After agitation for three hours at room temperature, the precipitate is filtered with suction and purified by crystallisation in diluted ethanol (melting point: 204°-206° C.; yield 4.6 g(79%).

| Analysis: $C_{10}H_9ClN_2O_2$ | | | |
|---|---|---|---|
| Calculated: | C % 53.46 | H% 4.04 | N % 12.47 |
| Found: | 53.41 | 4.07 | 12.52 |

As far as is known, this compound is not described in the literature.

EXAMPLE XIII 1-methyl 1,2,4,5-tetrahydro 2,4-diketo 3H-1,5-benzodiazepine ($R_1$ = H, $R_2$ = H, $R_3$ = H, $R_4$ = $CH_3$)

13.3 g of N-methyl-N-carbethoxy acetyl-o-nitroaniline(melting point: 54-55° C. after recrystallisation in petroleum ether), obtained in the example I, are admixed with 19.5 g of powdered zinc. The mixture is suspended, while stirring, in diluted hydrochloric acid (75 c.c. of concentrated hydrochloric acid, mixed with 250 c.c. of water). The temperature of the mass rises spontaneously up to 50° C., while anilide dissolves slowly. After about an hour, diazepine begins to separate out, is filtered with suction and crystallised in water, Melting point: 240°-242° C.

| Analysis: $C_{10}H_{10}N_2O_2$ | | | |
|---|---|---|---|
| Calculated: | C % 63.14 | H % 5.30 | N % 14.73 |
| Found: | 62.61 | 5.20 | 14.15 |

As far as is known, this compound is not described in the literature.

EXAMPLE XIV 1-methyl 5-isopropyl 1,2,4,5-tetrahydro 2,4-diketo3H-1,5-benzodiazepine

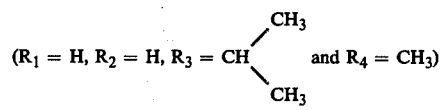

($R_1$ = H, $R_2$ = H, $R_3$ = CH$\diagup_{CH_3}^{CH_3}$ and $R_4$ = $CH_3$)

11.4 g of 1-methyl 1,2,4,5-tetrahydro 2,4-diketo 3H-1,5-benzodiazepine, obtained in the example XIII, and 16 g of isopropyl iodide are added to an alcoholic solution of sodium ethylate, obtained by reacting 1.4 g of sodium in 100 cc of anhydrous ethanol. The mixture is refluxed for twenty-five hours, then the solvent is completely evaporated under reduced pressure and the residue is taken up in 150 ml of a 10% solution of caustic soda. After agitation, the undissolved part is filtered with suction and crystallised is isopropanol. Yield: 5.3 g: melting point: 153°-160° C.

| Analysis: $C_{13}H_{16}N_2O_2$ | | | |
|---|---|---|---|
| Calculated: | C % 67.27 | H % 6.94 | N % 12.06 |
| Found: | 66.97 | 6.89 | 11.02 |

3.7 g of starting product are recovered from the mother-liquors.

As far as is known, this compound is not described in the literature.

EXAMPLE XV 1,5-dimethyl 1,2,4,5-tetrahydro 2,4-diketo 3H-1,5-benzodiazepine ($R_1$ = H, $R_2$ = H, $R_3$ = $CH_3$, $R_4$ = $CH_3$ )

2 g of sodium amide are added to a suspension of 9.5 g of 1-methyl 1,2,4,5-tetrahydro 2,4-diketo 3H-1,5-benzodiazepine, obtained in the example XIV, in 30 c.c. of xylene, and the whole is heated for about thirty minutes, while agitating, treated with 20 c.c. of methyl-sulfate and as soon as the exothermic reaction has ceased, this is heated and boiled for three hours. The solvent is evaporated under reduced presure, the residue is taken up in 200 c.c. of a 10% solution of caustic soda, and after agitation, suction filtered, and purified upon crystallisation in 90% ethanol. Yield 4.5 g; melting point: 240°-242° C.

| Analysis: $C_{11}H_{12}N_2O_2$ | | | |
|---|---|---|---|
| Calculated: | C % 64.69 | H % 5.92 | N % 13.72 |
| Found: | 64.67 | 6.12 | 13.95 |

As far as is known, this compound is not described in the literature.

EXAMPLE XVI 1-methyl 5-butyl 1,2,4,5-tetrahydro 2,4-diketo 3H-1,5-benzodiazepine ($R_1$ and $R_2$ = H, $R_3$ = $C_4H_9$, $R_5$ = $CH_3$)

From 1-methyl 1,2,4,5-tetrahydro 2,4-dioxo 3H-1,5-benzodiazepine (obtained in the example XIII), by action of butyl halide and recrystallisation of the butylated product in 50% ethanol, there is obtained 1-methyl 5-n-butyl 1,2,4,5-tetrhydro 2,4-dioxo 3H-1,5-benzodiazepine m.p. 141°–143° C.

| Analysis: $C_{14}H_{18}N_2O_2$ | | | |
|---|---|---|---|
| Calculated: | C % 68.27 | H % 7.37 | N % 11.38 |
| Found: | 68.02 | 7.24 | 11.60 |

As far as is known, this compound is not described in the literature.

EXAMPLE XVII 1-methyl 7-methoxy 1,2,4,5-tetrahydro 2,4-dioxo 3H-1,5-benzodiazepine ($R_1$= $OCH_3$, $R_2$ = H, $R_3$= $CH_3$)

Starting from N-carbethoxy acetyl N-methyl-1-methoxy o-phenylene diamine, obtained in the example IV, there is obtained, by action of hydrochloric acid, 1-methyl 7-methoxy 1,2,4,5-tetrahydro 2,4-dioxo 3H-1,5-benzodiazepine, melting at 201°–203° C. after recrystallisation in 80% isopropanol.

| Analysis: $C_{11}H_{12}N_2O_3$ | | | |
|---|---|---|---|
| Calculated: | C % 59.99 | H % 5.49 | N % 12.72 |
| Found: | 60.11 | 5.60 | 12.80 |

As far as is known, this compound is not described in the literature.

EXAMPLE XVIII 1-phenyl 5-(cyclopropyl methyl)8-chloro 1,2,4,5-tetrahydro 2,4-dioxo 3H-1,5-benzodiazepine ($R_1$ = H, $R_2$=Cl,

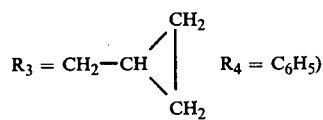

$R_4$ = $C_6H_5$)

Starting from 1-phenyl 8-chloro 1,2,4,5-tetrahydro 2,4-dioxo 3H-1,5-benzodiazepine, obtained according to the example X, and by acting a (cyclopropyl) methyl halide in the presence of a basic agent, there is obtained 1-phenyl 5-(cyclopropyl) methyl 8-chloro 1,2,5,5-tetrahydro 2,4-dioxo 3H-1,5-benzodiazepine, melting at 215°–218° C. after recrystallisation in ethanol.

| Analysis: $C_{19}H_{17}N_2ClO_2$ | | | |
|---|---|---|---|
| Calculated: | C % 66.96 | H % 5.03 | N % 8.22 |
| Found: | 66.88 | 5.08 | 7.92 |

As far as is known, this compound is not described in the literature.

EXAMPLE XIX

In the same manner, by acting allyl bromide or chloride on 1-phenyl 8-chloro 1,2,4,5-tetrahydro 2,4-dioxo 3H-1,5-benzodiazepine, there is obtained 1-phenyl 5-allyl 8-chloro 1,2,4,5-tetrahydro 2,4-dioxo 3H-1,5-benzodiazepine ($R_1$ = H, $R_2$ = Cl, $R_3$ = $CH_2$—CH = $CH_2$, $R_4$ = $C_6H_5$) melting at 199°–201° C. after recrystallisation in 70% ethanol.

| Analysis: $C_{18}H_{15}ClN_2O_2$ | | | |
|---|---|---|---|
| Calculated: | C % 66.15 | H % 4.63 | N % 8.57 |
| Found: | 66.00 | 4.34 | 8.36 |

As far as is known, this compound is not described in the literature.

EXAMPLE XX

In the same manner, by acting ethyl bromide or iodide in the presence of sodium ethylate on 1-phenyl 8-chloro 1,2,4,5-tetrahydro 2,4-dioxo 3H-1,5-benzodiazepine, there is obtained 1-phenyl 5-ethyl 8-chloro 1,2,4,5-tetrahydro 2,4-dioxo 3H-1,5-benzodiazepine ($R_1$ = H, $R_2$ = Cl, $R_3$ = $C_2H_5$, $R_4$ = $C_6H_5$), melting at 220°–222° C. upon recrystallisation in ethanol.

| Analysis: $C_{17}H_{15}ClN_2O_2$ | | | |
|---|---|---|---|
| Calculated: | C % 64.86 | H % 4.80 | N % 8.90 |
| Found: | 65.14 | 4.58 | 8.96 |

As far as is known, this compound is not described in the literature.

EXAMPLE XXI

In the same manner, by acting propyl bromide or iodide in the presence of sodium ethylate, starting from 1-phenyl 8-chloro 1,2,4,5-tetrahydro 2,4-dioxo 3H-1,5-benzodiazepine, there is obtained 1-phenyl 5-propyl 8-chloro 1,2,4,5-tetrahydro 3H-1,5-benzodiazepine ($R_1$ = H, $R_2$ = Cl, $R_3$ = $C_3H_7$, $R_4$ = $C_6H_5$) melting at 192°–194° C. upon recrystallisation in ethanol.

| Analysis: $C_{18}H_{17}OlN_2O_2$ | | | |
|---|---|---|---|
| Calculated: | C % 65.75 | H % 5.21 | N % 8.52 |
| Found: | 55.66 | 5.12 | 8.60 |

As far as is known this compound is not described in the literature.

EXAMPLE XXII

In the same manner, by acting butyl bromide in the presence of sodium ethylate, starting from 1-phenyl 8-chloro 1,2,4,5-tetrahydro 2,4-dioxo 3H-1,5-benzodiazepine, there is obtained 1-phenyl 5-butyl 8-chloro 1,2,4,5-tetrahydro 3H-1,5-benzodiazepine ($R_1$ = H, $R_2$ = Cl, $R_3$ = $C_4H_9$, $R_4$ = $C_6H_5$) melting at 159°–161° C., upon recrystallisation in 50% ethanol.

| Analysis: $C_{19}H_{19}ClN_2O_2$ | | | |
|---|---|---|---|
| Calculated: | C % 66.57 | H % 5.59 | N % 8.17 |
| Found: | 66.29 | 5.44 | 7.98 |

As far as is known this compound is not described in the literature.

EXAMPLE XXIII

In the same manner, by acting (2'-methylallyl) chloride or bromide in the presence of a metallation agent, starting from 1-phenyl 8-chloro 1,2,4,5-tetrahydro 2,4-dioxo 3H-1,5-benzodiazepine, there is obtained 1-phenyl 5-(2'-methylallyl) 8-chloro 1,2,4,5-tetrahydro 2,4-dioxo 3H-1,5-benzodiazepine ($R_1 = H$, $R_2 = Cl$, $R_3 =$

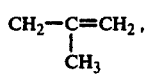

$R_4 = C_6H_5$) melting at 149°–151° C. upon recrystallisation in 50% ethanol.

As far as is known, this compound is not described in the literature.

What we claim is:
1. N-carbalkoxy-acetyl aniline of the formula

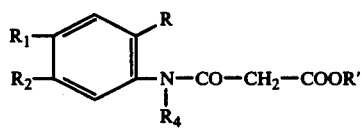

wherein
R is $-NO_2$ or $-NH_2$
$R_1$ and $R_2$ are hydrogen, halogen, hydroxy, methoxy or carboxy esterified with an alkanol having 1 to 3 carbon atoms,
$R_4$ is methyl, phenyl or p-tolyl
R' is alkyl having 1 to 4 carbon atoms.
2. N-carbalkoxy-acetyl-o-nitro aniline according to claim 1 of the formula

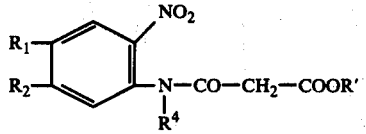

wherein
$R_1$ and $R_2$ are hydrogen, halogen, hydroxy, methoxy or carboxy esterified with an alkanol having 1 to 3 carbon atoms,
$R_4$ is methyl
R' is alkyl having 1 to 4 carbon atoms.
3. N-carbalkoxy-acetyl-o-amino aniline according to claim 1 of the formula

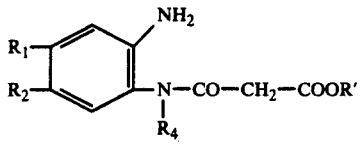

wherein
$R_1$ and $R_2$ are hydrogen, halogen, hydroxy, methoxy or carboxy esterified with an alkanol having 1 to 3 carbon atoms,
$R_4$ is methyl
R' is alkyl having 1 to 4 carbon atoms.
4. N-carbalkoxy-acetyl aniline of the formula

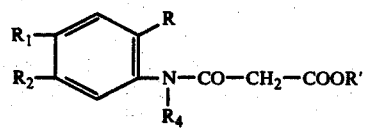

wherein
R is amino or nitro,
$R_1$ is halogen, hydroxy, methoxy or carboxy esterified with an alkanol having 1 to 3 carbon atoms,
$R_2$ is hydrogen,
$R_4$ is methyl,
or wherein
R is amino or nitro
$R_1$ is hydrogen,
$R_2$ is hydrogen, halogen, hydroxy, methoxy or carboxy esterified with an alkanol having 1 to 3 carbon atoms,
$R_4$ is phenyl,
R' is alkyl having from 1 to 4 carbon atoms.
5. N-carbalkoxy-acetyl-o-amino aniline according to claim 4 of the formula

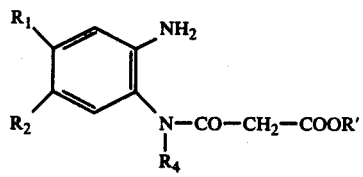

wherein
$R_1$ is halogen, hydroxy, methoxy or carboxy esterified with an alkanol having 1 to 3 carbon atoms,
$R_2$ is hydrogen,
$R_4$ is methyl,
or wherein $R_1$ is hydrogen,
$R_2$ is hydrogen, halogen, hydroxy, methoxy or carboxy esterified with an alkanol having 1 to 3 carbon atoms,
$R_4$ is phenyl,
R' is alkyl having from 1 to 4 carbon atoms.
6. N-carbalkoxy-acetyl-o-nitro aniline according to claim 4 of the formula

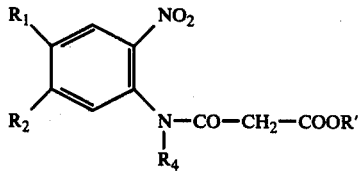

wherein
$R_1$ is halogen, hydroxy, methoxy or carboxy esterified with an alkanol having 1 to 3 carbon atoms,
$R_2$ is hydrogen,
$R_4$ is methyl,
or wherein $R_1$ is hydrogen, R$_2$ is hydrogen, halogen, hydroxy, methoxy or carboxy esterified with an alkanol having 1 to 3 carbon atoms, R$_4$ is phenyl, R' is alkyl having from 1 to 4 carbon atoms.

7. N-carbethoxyacetyl-N-phenyl-5-chloro-o-phenylene diamine.

8. N-carbethoxyacetyl-2-nitro-5-chloro-diphenylamine.

9. A process for the preparation of N-carbalkoxyacetyl-o-nitro aniline of the general formula defined in claim 1, in which a corresponding o-nitro aniline of the general formula

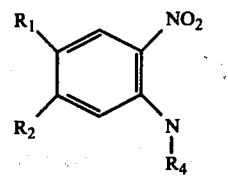

wherein R$_1$, R$_2$ and R$_4$ are as defined in claim 8, is condensed in an inert solvent with a malonic mono-ester or a functional derivative of its acid function to give the desired N-carbalkoxyacetyl o-nitro aniline.

* * * * *

UNITED STATES PATENT OFFICE
CERTIFICATE OF CORRECTION

Patent No. 4,138,572    Dated February 6, 1979

Inventor(s) Silvano ROSSI

It is certified that error appears in the above-identified patent and that said Letters Patent are hereby corrected as shown below:

Column 2, line 48, change "lenic" to -- lonic --;

Column 3, the first formula should be as follows:

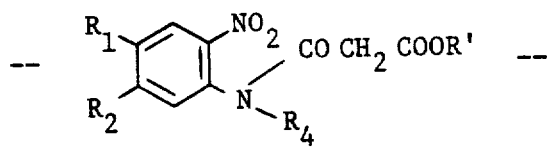

Column 3, line 18, change "S-aryl" to -- "N-aryl --;

Column 8, line 61, change "12 4.56" to -- 4.56 --;

Column 10, line 48, change "d-methoxy" to -- 4-methoxy --;

Column 10, line 50, change "cme." to -- cc. --;

Column 10, line 58, change "omission" to -- emission --;

Column 11, line 7, change "methylamino)" to -- N-methylamino) --;

Column 11, line 58, change "$R_4 = O_6H_5$" to -- $R_4 = C_6H_5$ --;

Column 11, line 62, change "$R' = O_2H_5$)" to -- $R' = C_2H_5$) --;

Column 12, line 2, change "H % 4.50" to -- H % 4.80 --;

Column 12, line 13, change "$R_4 = O_6H_5$) to -- $R_4 = C_6H_5$) --;

Column 12, line 37, change "= $OH_5$, $R_4$" to -- = $CH_3$, $R_4$ --;

Column 12, line 38, change "= $O_6H_5$)" to -- = $C_6H_5$) --;

Column 12, line 48, change "H % 5.50" to -- H % 5.30 --;

Column 12, line 58, change "$R_4 = O_6H_5$)" to -- $R_4 = C_6H_5$) --;

Column 13, line 17, change "a halide" to -- a methyl halide --;

UNITED STATES PATENT OFFICE
CERTIFICATE OF CORRECTION

Patent No. 4,138,572　　　　　　　　　　Dated　February 6, 1979

Inventor(s) Silvano ROSSI

It is certified that error appears in the above-identified patent and that said Letters Patent are hereby corrected as shown below:

Column 14, line 44, change "11.02" to -- 11.82 --;

Column 15, line 33, after "$R_3 =$" insert -- H, --;

Column 15, line 34, before "$CH_3$)" insert -- $R_4 =$ --;

Column 15, line 35, change "N-methyl-1-" to -- N-methyl-4- --;

Column 15, line 66, change "1,2,5,5-tet-" to -- 1,2,4,5-tet- --;

Column 16, line 53, change "$C_{18}H_{17}O1N_2O_2$" to -- $C_{18}H_{17}ClN_2O_2$ --;

Column 16, line 55, change "55.66" to -- 65.66 --;

Column 16, line 55, change "5.12" to -- 5.17 --;

Column 20, line 9, change "claim 8" to -- claim 6 --.

Column 11, line 63, change "VI" to -- V --;

Column 12, line 40, change "VIII" to -- VII --;

Column 13, line 17, change "XI" to -- X --;

Column 13, line 18, change "X" to -- IX --;

Column 13, line 24, change "XI" to -- X --;

Column 13, line 25, change "IX" to -- VIII --;

Column 14, line 58, change "XIV" to -- XIII --.

Signed and Sealed this

Twenty-third Day of October 1979

[SEAL]

Attest:

RUTH C. MASON
Attesting Officer

LUTRELLE F. PARKER
Acting Commissioner of Patents and Trademarks